US011209644B1

(12) United States Patent
Fu et al.

(10) Patent No.: US 11,209,644 B1
(45) Date of Patent: Dec. 28, 2021

(54) PUPIL STEERING FOR A PUPIL EXPANDER

(71) Applicant: Facebook Technologies, LLC, Menlo Park, CA (US)

(72) Inventors: Yijing Fu, Redmond, WA (US); Lu Lu, Kirkland, WA (US); Mengfei Wang, Seattle, WA (US)

(73) Assignee: FACEBOOK TECHNOLOGIES, LLC, Menlo Park, CA (US)

( * ) Notice: Subject to any disclaimer, the term of this patent is extended or adjusted under 35 U.S.C. 154(b) by 416 days.

(21) Appl. No.: 16/100,850

(22) Filed: Aug. 10, 2018

(51) Int. Cl.
*G06F 3/01* (2006.01)
*G02B 27/01* (2006.01)
*G02F 1/01* (2006.01)
*G02B 27/00* (2006.01)
*F21V 8/00* (2006.01)
*A61B 3/11* (2006.01)
*G02B 27/42* (2006.01)

(52) U.S. Cl.
CPC .......... *G02B 27/0081* (2013.01); *A61B 3/112* (2013.01); *G02B 6/0016* (2013.01); *G02B 27/0172* (2013.01); *G02B 6/0035* (2013.01); *G02B 27/4205* (2013.01); *G02B 2027/0123* (2013.01); *G02B 2027/0174* (2013.01); *G02B 2027/0178* (2013.01)

(58) Field of Classification Search
CPC ............ G02B 27/0081; G02B 27/0172; G02B 6/0016; G02B 2027/0187; G02B 2027/0138; G02B 2027/0178; G02B 27/0093; A61B 3/112; G02F 1/011; G06F 3/0346; G06F 3/013
See application file for complete search history.

(56) References Cited

U.S. PATENT DOCUMENTS

| | | | |
|---|---|---|---|
| 8,466,953 | B2 | 8/2013 | Levola |
| 10,775,633 | B1* | 9/2020 | Lee .................... G02B 27/0179 |
| 2017/0102543 | A1 | 4/2017 | Vallius |
| 2017/0315347 | A1 | 11/2017 | Juhola et al. |
| 2017/0357055 | A1 | 12/2017 | Spector et al. |
| 2018/0284884 | A1* | 10/2018 | Sulai ....................... G02F 1/011 |

FOREIGN PATENT DOCUMENTS

| | | |
|---|---|---|
| CN | 105692691 | 6/2016 |
| WO | 2009077803 | 6/2009 |
| WO | 2018031634 | 2/2018 |

* cited by examiner

*Primary Examiner* — Jack Dinh
(74) *Attorney, Agent, or Firm* — Weaver Austin Villeneuve & Sampson LLP (57) ABSTRACT

A pupil expander spatially modulates decoupling efficiency of light for pupil steering. The pupil expander can be used in a waveguide display, such as part of an artificial-reality display, to reduce power consumption of an optical source.

20 Claims, 9 Drawing Sheets

PUPIL STEERING FOR A PUPIL EXPANDER

BACKGROUND

This disclosure relates generally to near-eye-display systems, and more specifically to waveguide displays. Conventional near-eye displays generally have a display element that generates image light that passes through one or more lenses before reaching a user's eye. Additionally, near-eye displays in virtual-reality (VR) systems and/or augmented-reality (AR) systems have design criteria to be compact, be light weight, and provide two-dimensional expansion with a large eye box and a wide field-of-view (FOV). Traditionally, VR displays are magnifier optics displays. A computer generates an image, and optics are used to magnify the image. It is challenging to design near-eye displays to achieve a small form factor, a large FOV, and/or a large eye box.

SUMMARY

The present disclosure relates to pupil steering in a pupil expander.

BRIEF DESCRIPTION OF THE DRAWINGS

Illustrative embodiments are described with reference to the following figures.

The figures depict embodiments of the present disclosure for purposes of illustration only. One skilled in the art will readily recognize from the following description that alternative embodiments of the structures and methods illustrated may be employed without departing from the principles, or benefits touted, of this disclosure.

In the appended figures, similar components and/or features may have the same reference label. Further, various components of the same type may be distinguished by following the reference label by a dash and a second label that distinguishes among the similar components. If only the first reference label is used in the specification, the description is applicable to any one of the similar components having the same first reference label irrespective of the second reference label.

DETAILED DESCRIPTION

In the following description, for the purposes of explanation, specific details are set forth in order to provide a thorough understanding of certain inventive embodiments. However, it will be apparent that various embodiments may be practiced without these specific details. The figures and description are not intended to be restrictive.

This disclosure relates to pupil steering in a waveguide display for an augmented-reality (AR) system. A near-eye display system uses pupil expansion to overcome concerns of proper eye relief. The waveguide display comprises a grating structure to out couple light from a waveguide. However, brightness of the AR system drops because of pupil expansion and diffraction efficiency of the grating structure. To achieve certain brightness levels, selection of light sources is limited and/or power consumption is increased.

To more efficiently maintain brightness, pupil steering in the waveguide is used. For pupil expansion, the exit pupil of the optical system is expanded so that an entrance pupil of a human eye is within the exit pupil of the AR system, regardless of IPD (inter pupil distance) and/or gaze angle of the eye. However, to achieve this target, a static exit pupil of the optical system has to be significantly larger than the entrance pupil of the human eye (in order to accommodate a range of different IPDs and/or gaze angles), which means some of the light is wasted. In accordance with embodiments of the present disclosure utilizing pupil steering, the exit pupil of the optical system may be only slightly larger than the entrance pupil of the human eye. However, the exit pupil is not static and can be moved around (i.e., steered) based on a position and gaze angle of the eye, which can be determined by an eye-tracking system. With pupil steering, less light is wasted and a user can still see the content of a displayed image.

To pupil steer, a liquid crystal (LC) layer can be disposed in the waveguide display. The LC layer is used to modulate diffraction efficiency of light in the waveguide as a function of space and time. The LC layer is sandwiched between two glass layers. For areas that are in a region of the waveguide display that will not have light exit toward an eye of a user, as determined based on eye tracking of the user, the LC layer is modulated to decrease diffraction efficiency of light impinging on the grating structure at a region of the waveguide display that will not have light exit toward the eye of the user.

Figure 1:
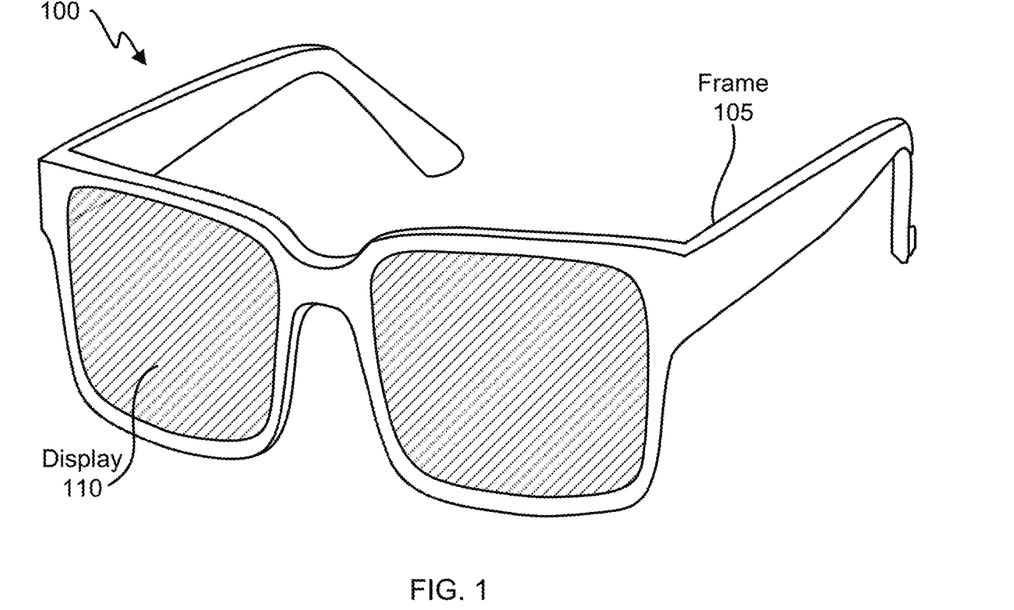
FIG. 1 is a diagram of an embodiment of a near-eye display.

FIG. 1 is a diagram of an embodiment of a near-eye display 100. The near-eye display 100 presents media to a user. Examples of media presented by the near-eye display 100 include one or more images, video, and/or audio. In some embodiments, audio is presented via an external device (e.g., speakers and/or headphones) that receives audio information from the near-eye display 100, a console, or both, and presents audio data based on the audio information. The near-eye display 100 is generally configured to operate as a virtual reality (VR) display. In some embodiments, the near-eye display 100 is modified to operate as an augmented reality (AR) display and/or a mixed reality (MR) display.

The near-eye display 100 includes a frame 105 and a display 110. The frame 105 is coupled to one or more optical elements. The display 110 is configured for the user to see content presented by the near-eye display 100. In some embodiments, the display 110 comprises a waveguide display assembly for directing light from one or more images to an eye of the user.

Figure 2:
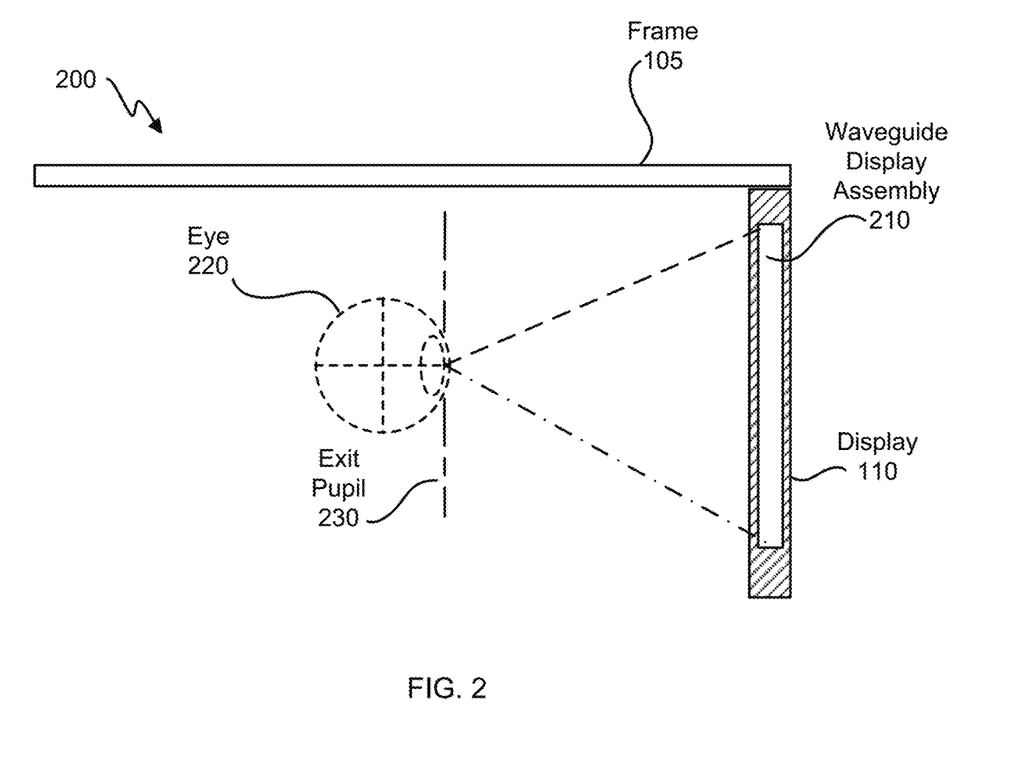
FIG. 2 is an embodiment of a cross section of the near-eye display.

FIG. 2 is an embodiment of a cross section 200 of the near-eye display 100 illustrated in FIG. 1. The display 110 includes at least one waveguide display assembly 210. An exit pupil 230 is a location where the eye 220 is positioned in an eye box region when the user wears the near-eye display 100. For purposes of illustration, FIG. 2 shows the cross section 200 associated with an eye 220 and a waveguide display assembly 210; a second waveguide display assembly is used for a second eye of a user.

The waveguide display assembly 210 is configured to direct image light to an eye box located at the exit pupil 230 and to the eye 220. The waveguide display assembly 210 may be composed of one or more materials (e.g., plastic, glass, etc.) with one or more refractive indices. In some embodiments, the near-eye display 100 includes one or more optical elements between the waveguide display assembly 210 and the eye 220. In some embodiments, the waveguide display assembly 210 includes one or more waveguide displays to generate a singular view to a user.

Figure 3:
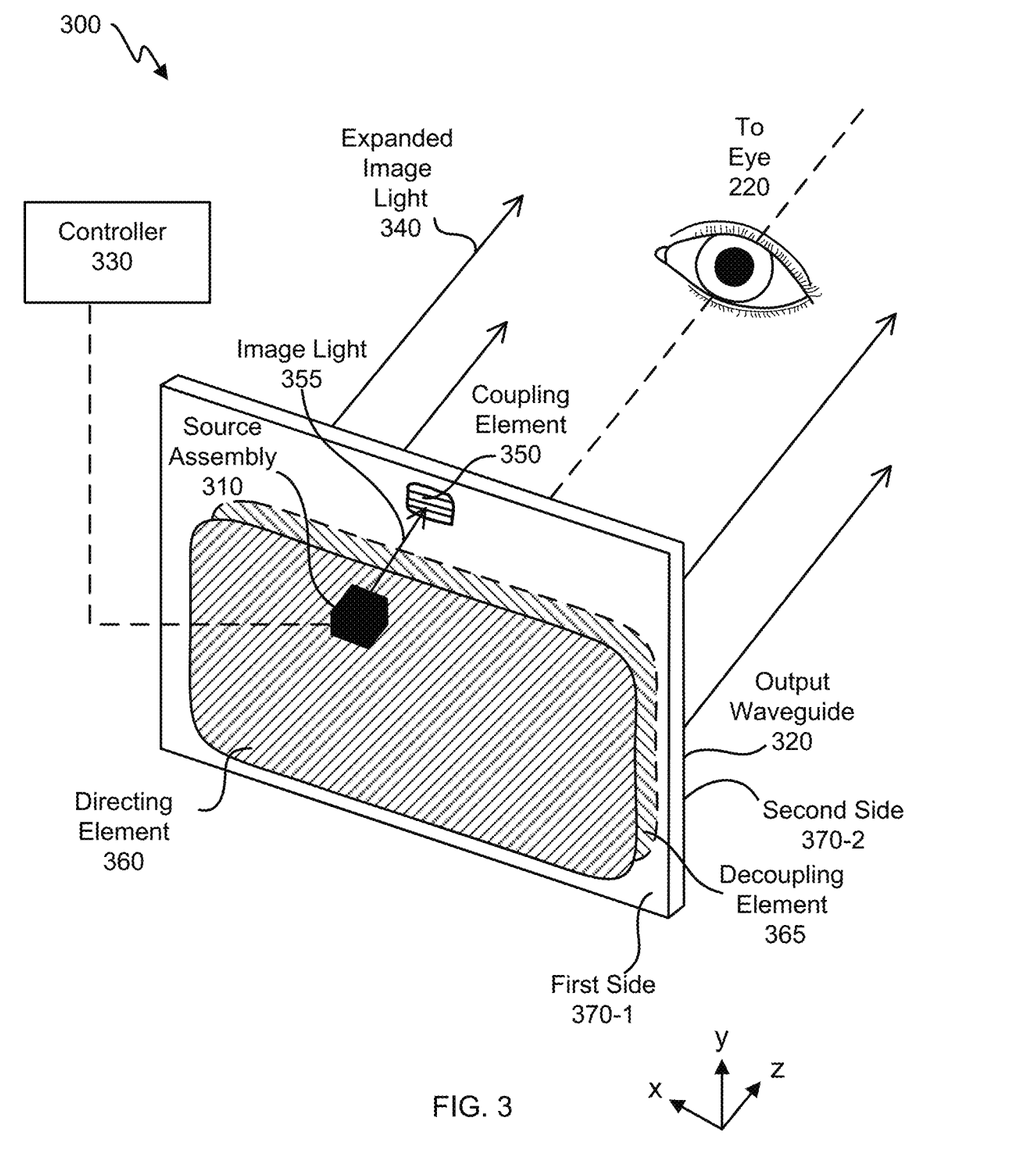
FIG. 3 illustrates an isometric view of an embodiment of a waveguide display.

FIG. 3 illustrates an isometric view of an embodiment of a waveguide display 300. In some embodiments, the waveguide display 300 is a component of the waveguide display assembly 210 of the near-eye display 100. In some embodiments, the waveguide display 300 is part of some other near-eye display or other system that directs image light to a particular location.

The waveguide display 300 includes a source assembly 310, an output waveguide 320, and a controller 330. For purposes of illustration, FIG. 3 shows the waveguide display 300 associated with a single eye 220, but in some embodiments, another waveguide display, whether separate or partially separate from the waveguide display 300, provides image light to another eye of the user.

The source assembly 310 generates image light 355. The source assembly 310 generates and outputs the image light 355 to a coupling element 350 located on a first side 370-1 of the output waveguide 320. The output waveguide 320 is an optical waveguide that outputs expanded image light 340 to an eye 220 of a user. The output waveguide 320 receives the image light 355 at one or more coupling elements 350 located on the first side 370-1 and guides received input image light 355. In some embodiments, the coupling element 350 couples the image light 355 from the source assembly 310 into the output waveguide 320. The coupling element 350 may be, e.g., a diffraction grating, a holographic grating, one or more cascaded reflectors, one or more prismatic surface elements, a metalens, a refractive surface at an angle with or without optical power, and/or an array of holographic reflectors.

Light from the output waveguide 320 is coupled out of the output waveguide 320 using a decoupling element 365. Expanded image light 340 decoupled from the output waveguide 320 is transmitted to the eye 220 of a user. In some embodiments, a directing element 360 is used to redirect light in the output waveguide 320 to the decoupling element 365. The directing element 360 is part of, or affixed to, the first side 370-1 of the output waveguide 320. The decoupling element 365 is part of, or affixed to, the second side 370-2 of the output waveguide 320, such that the directing element 360 is opposed to the decoupling element 365. The directing element 360 and/or the decoupling element 365 may be, e.g., a diffraction grating, a holographic grating, one or more cascaded reflectors, one or more prismatic surface elements, a Bragg grating, and/or an array of holographic reflectors. In some embodiments, the directing element 360 can be similar to the decoupling element 365, the directing element 360 can be part of the decoupling element 365, the directing element 360 can be on the second side 370-2, the decoupling element 365 can be on the first side 370-1, the directing element 360 and/or the decoupling element 365 can be between the first side 370-1 and the second side 370-2, and/or the directing element 360 and/or the decoupling element 365 can be outside of the output waveguide 320 (e.g., adjacent to the output waveguide 320).

The second side 370-2 represents a plane along an x-dimension and a y-dimension. The output waveguide 320 may be composed of one or more materials that facilitate total internal reflection of the image light 355 with a transparency in wavelength bands of interest. The output waveguide 320 may be composed of plastic, glass, and/or polymers. The output waveguide 320 has a relatively small form factor. For example, the output waveguide 320 may be approximately 50 millimeters (mm) wide along an x-dimension; 30 mm long along a y-dimension; and 0.3 to 5.0 mm thick along a z-dimension.

In some embodiments, the waveguide display 300 comprises multiple output waveguides 320. For example, waveguide display 300 comprises a stacked waveguide display. The stacked waveguide display is a polychromatic display that can be projected on multiple planes (e.g. multi-planar colored display; a red-green-blue (RGB) display created by stacking output waveguides 320 used for different colors). The stacked waveguide display can comprise three output waveguides 320, one output waveguide 320 for red light, one output waveguide 320 green light, and one output waveguide 320 blue light (sometimes referred to as a waveguide stack). In some configurations, two output waveguides 320 are used (e.g., a "red" waveguide and a "blue" waveguide, where "green" is shared between the red waveguide and the blue waveguide). In some configurations, the stacked waveguide display is a monochromatic display that can be projected on multiple planes (e.g. multi-planar monochromatic display). In some configurations, the waveguide display 300 is a varifocal waveguide display. The varifocal waveguide display is a display that can adjust a focal position of image light emitted from the waveguide display. In some embodiments, the waveguide display assembly 210 may include the stacked waveguide display and the varifocal waveguide display. In some embodiments, a single output waveguide 320 is used for a wide spectrum of light. For example, a Bragg grating is used as the decoupling element 365 and out couples red, green, and blue light from the output waveguide 320.

The controller 330 controls light emitted from the source assembly 310. For example, the controller 330 controls scanning operations of the source assembly 310 and/or timing of light sources turning off and on. The controller 330 can determine scanning instructions for the source assembly 310. The controller 330 can be used to control full-field projector engines. In some embodiments, the output waveguide 320 outputs expanded image light 340. The expanded image light 340 provides an expanded eyebox (relative to a pupil area of the source assembly 310) with a large field of view (FOV) to the user's eye 220. For example, expanded image light 340 is provided to the user such that the waveguide display 300 provides a field of view equal to or greater than 60 degrees and equal to or less than 150 degrees in x and/or y. The output waveguide 320 is configured to provide an eye box with a length equal to or greater than 10 mm and equal to or less than 50 mm in x and/or y. The controller 330 can be used in conjunction with a graphics engine to render image information based on sensors measuring head and/or eye location.

Figure 4:
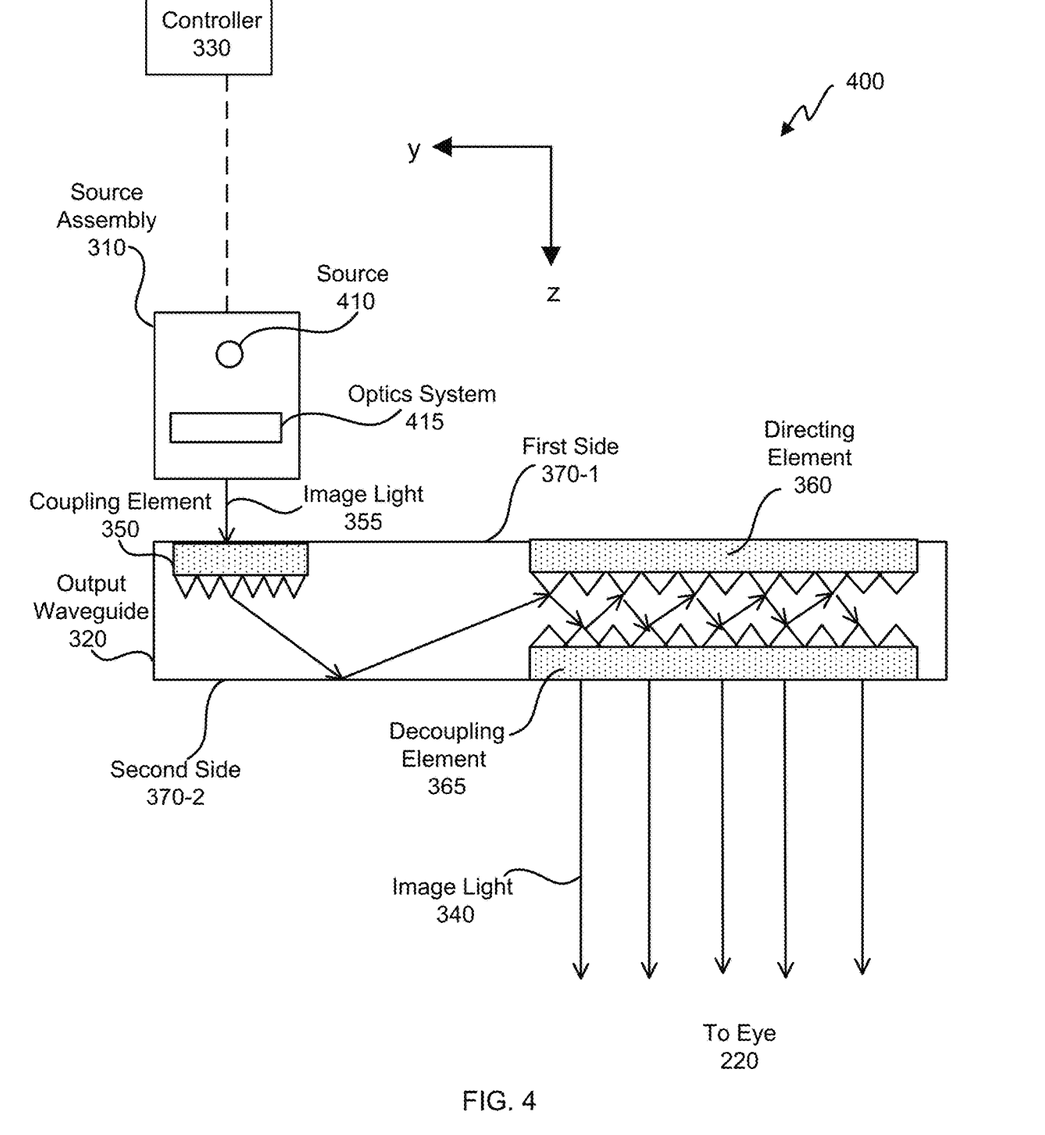
FIG. 4 illustrates a cross section of an embodiment of the waveguide display.

FIG. 4 illustrates an embodiment of a cross section 400 of the waveguide display 300. The cross section 400 includes the source assembly 310 and the output waveguide 320. The source assembly 310 generates image light 355 in accordance with instructions from the controller 330. The source assembly 310 includes a source 410 and an optics system 415. The source 410 is a light source that generates coherent, partially coherent, and/or incoherent light. The source 410 may be a laser diode, a vertical cavity surface emitting laser, a liquid-crystal-on-silicon, a superluminescent diode, and/or an organic or inorganic light emitting diode array (either through spatial or temporal control).

The optics system 415 includes one or more optical components that condition the light from the source 410. Conditioning light from the source 410 may include, e.g., expanding, collimating, and/or adjusting orientation in accordance with instructions from the controller 330. The one or more optical components may include one or more lens, liquid lens, mirror, freeform element, aperture, and/or grating. Light emitted from the optics system 415 (and also the source assembly 310) is sometimes referred to as image light 355.

The output waveguide 320 receives the image light 355. The coupling element 350 couples the image light 355 from the source assembly 310 into the output waveguide 320. In embodiments where the coupling element 350 is diffraction grating, a pitch of the diffraction grating is chosen such that total internal reflection occurs in the output waveguide 320, and the image light 355 propagates internally in the output waveguide 320 (e.g., by total internal reflection), toward the decoupling element 365. The directing element 360 redirects the image light 355 toward the decoupling element 365 for decoupling from the output waveguide 320.

In some embodiments, the directing element 360 and/or the decoupling element 365 are structurally similar. The expanded image light 340 exiting the output waveguide 320 is expanded along one or more dimensions (e.g., may be elongated along x-dimension). In some embodiments, the waveguide display 300 includes a plurality of source assemblies 310 and a plurality of output waveguides 320. Each of the source assemblies 310 emits a monochromatic image light of a specific band of wavelength corresponding to a color (e.g., red, green, or blue). Each of the output waveguides 320 may be stacked together with a distance of separation to output an expanded image light 340 that is multi-colored. In some embodiments, other color schemes are used (e.g., red, green, blue, green-blue). In some configurations, multiple source assemblies (e.g., 2 to 4 RGB source assemblies are used with 3 output waveguides 320, one red output waveguide, one green output waveguide, and one blue output waveguide).

Figure 5:
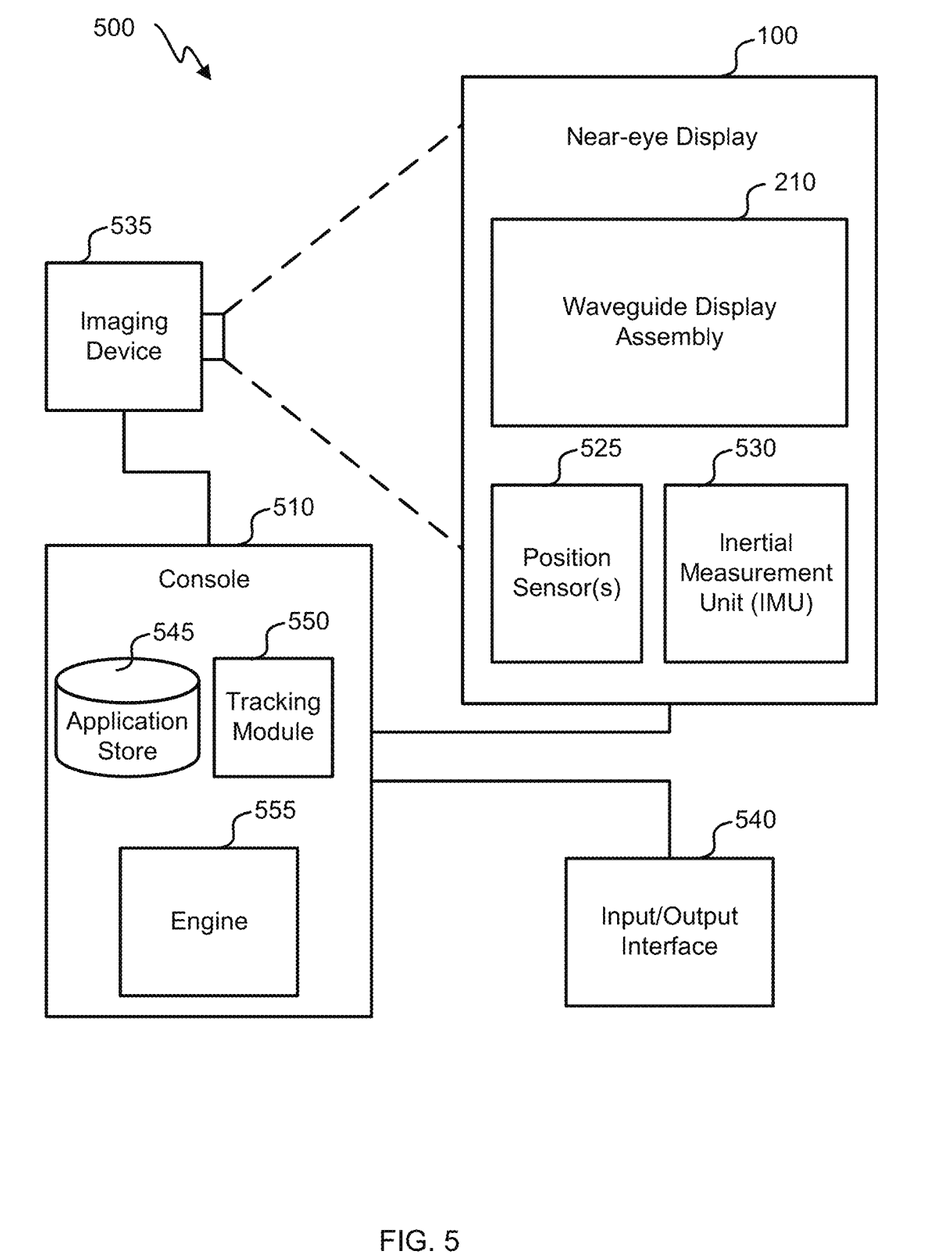
FIG. 5 is a block diagram of an embodiment of a system including the near-eye display.

FIG. 5 is a block diagram of an embodiment of a system 500 including the near-eye display 100. The system 500 comprises the near-eye display 100, an imaging device 535, and an input/output interface 540 that are each coupled to a console 510.

The near-eye display 100 is a display that presents media to a user. Examples of media presented by the near-eye display 100 include one or more images, video, and/or audio. In some embodiments, audio is presented via an external device (e.g., speakers and/or headphones) that receives audio information from the near-eye display 100 and/or the console 510 and presents audio data based on the audio information to a user. In some embodiments, the near-eye display 100 may also act as an AR eyewear glass. In some embodiments, the near-eye display 100 augments views of a physical, real-world environment, with computer-generated elements (e.g., images, video, sound, etc.).

The near-eye display 100 includes a waveguide display assembly 210, one or more position sensors 525, and/or an inertial measurement unit (IMU) 530. The waveguide display assembly 210 includes the source assembly 310, the output waveguide 320, and the controller 330. The IMU 530 is an electronic device that generates fast calibration data indicating an estimated position of the near-eye display 100 relative to an initial position of the near-eye display 100 based on measurement signals received from one or more of the position sensors 525. The imaging device 535 generates slow calibration data in accordance with calibration parameters received from the console 510. The imaging device 535 may include one or more cameras and/or one or more video cameras. The input/output interface 540 is a device that allows a user to send action requests to the console 510. An action request is a request to perform a particular action. For example, an action request may be to start or end an application or to perform a particular action within the application. The console 510 provides media to the near-eye display 100 for presentation to the user in accordance with information received from one or more of: the imaging device 535, the near-eye display 100, and the input/output interface 540. In the example shown in FIG. 5, the console 510 includes an application store 545, a tracking module 550, and an engine 555. The application store 545 stores one or more applications for execution by the console 510. An application is a group of instructions, that when executed by a processor, generates content for presentation to the user. Examples of applications include: gaming applications, conferencing applications, video playback application, or other suitable applications. The tracking module 550 calibrates the system 500 using one or more calibration parameters and may adjust one or more calibration parameters to reduce error in determination of the position of the near-eye display 100. The tracking module 550 tracks movements of the near-eye display 100 using slow calibration information from the imaging device 535. The tracking module 550 also determines positions of a reference point of the near-eye display 100 using position information from the fast calibration information.

The engine 555 executes applications within the system 500 and receives position information, acceleration information, velocity information, and/or predicted future positions of the near-eye display 100 from the tracking module 550. In some embodiments, information received by the engine 555 may be used for producing a signal (e.g., display instructions) to the waveguide display assembly 210 that determines a type of content presented to the user.

The coupling element 350, the output waveguide 320, and the decoupling element 365 (e.g., in FIG. 4) function as a pupil expander. Light from a small projector (e.g., source assembly 310) is expanded to an exit pupil, which is larger than light coming from the small projector. The pupil expander solves an eye-relief problem for a display system. However, brightness of the display system can significantly drop because of pupil expansion and/or diffraction efficiency of a grating structure used to decouple light out of the pupil expander. In some embodiments, a scanning-display system is used, which makes brightness an even larger concern because brightness is dropped by an amount of pixels that are created in a dimension of scanning. Not only can brightness be a problem, but power consumption, and/or the associated heat with the power consumption, can pose problems to designing a compact, portable near-eye display (e.g., one to be worn by a user).

To help resolve brightness and/or power consumption concerns, pupil steering in a pupil expander is used. Pupil steering is selectively decoupling light (e.g., from the output waveguide 320) to reduce decoupling light that likely won't be seen by a user. In some embodiments, diffraction efficiency of light incident on a grating is spatially modulated to provide pupil steering.

Figure 6:
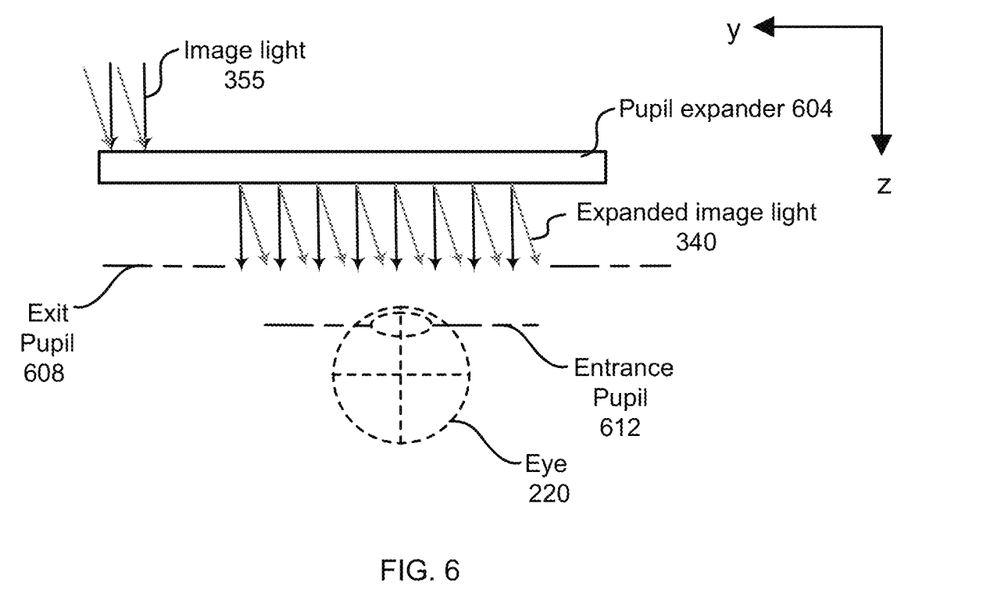
FIG. 6 is a simplified embodiment of a pupil expander.

FIG. 6 is a simplified embodiment of a pupil expander 604. Image light 355 from the source assembly 310 is coupled into the pupil expander 604. The pupil expander 604 can be a waveguide pupil expander. Other types of pupil expanders than a waveguide pupil expander can also be used. For pupil expansion, the exit pupil 608 of the pupil expander 604 is enlarged so that an entrance pupil 612 of a human eye (e.g., eye 220) is within the exit pupil 608, regardless of IPD (inter pupil distance) and/or gaze angle. However, to achieve this target, the exit pupil 608 of the pupil expander 604 has to be significantly larger than the entrance pupil 612 of the eye 220, which means a significant portion of light is wasted, and the optical system has low efficiency. For example, the eye 220 has an entrance pupil of about 2 to 3 mm. If the exit pupil 608 of the pupil expander 604 is several times the entrance pupil of the eye 220, such as 20 mm wide, then there will be a lot of expanded image light 340 that is wasted (e.g., up to 90% or greater loss).

Figure 7A:
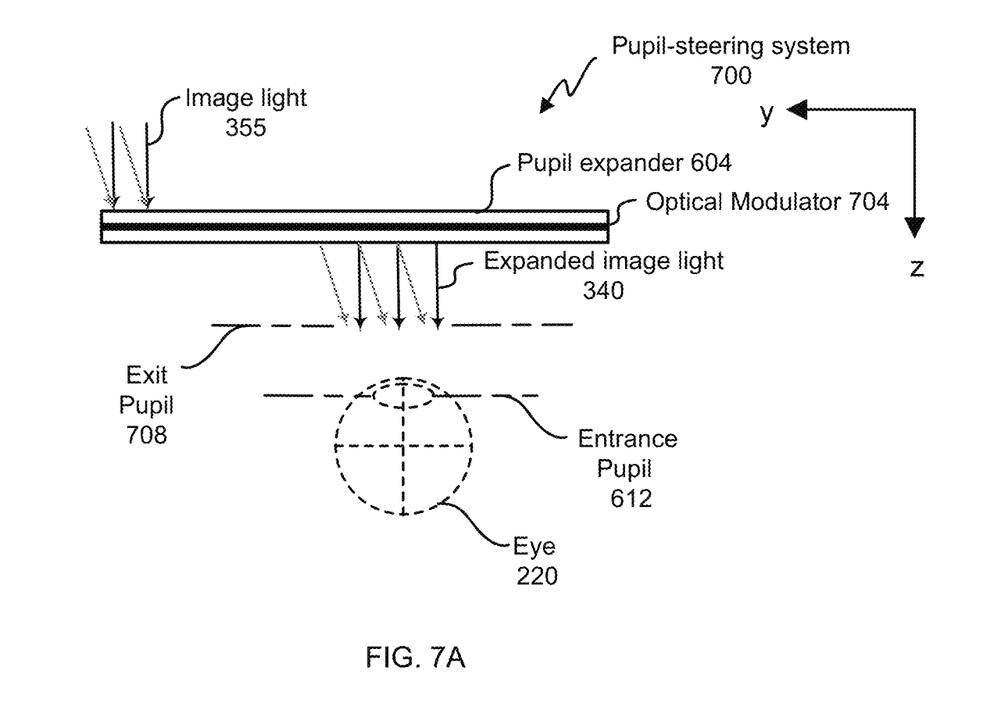
FIG. 7A is a simplified embodiment of a pupil expander with pupil steering.

FIG. 7A is a simplified embodiment of a pupil-steering system 700 having an optical modulator 704. For the pupil-steering system 700, an exit pupil 708 of the pupil-steering system 700 is not as large as the exit pupil 608. The exit pupil 708 is equal to or larger than the entrance pupil 612 of the eye 220 (e.g., equal to or greater than the entrance pupil 612 and/or equal to or less than 1.5, 2, 3, or 4 times the entrance pupil 612). Thus light is decoupled out of only a portion of the decoupling element 365. The exit pupil 708 can be steered around (e.g., in x and/or y) based on a position and/or a gaze angle of the eye 220. In some embodiments, eye tracking is used to determine the position and/or the gaze angle of the eye 220. By using pupil steering, less light is lost and the user can still see the content of the displayed image. Put another way, the exit pupil 608 can be a potential exit pupil area that the exit pupil 708 can be smaller than and/or steered around in (e.g., based on eye tracking). For example, at a given moment in time, a location of the exit pupil 708 in the potential exit pupil area depends on eye tracking.

Figure 7B:
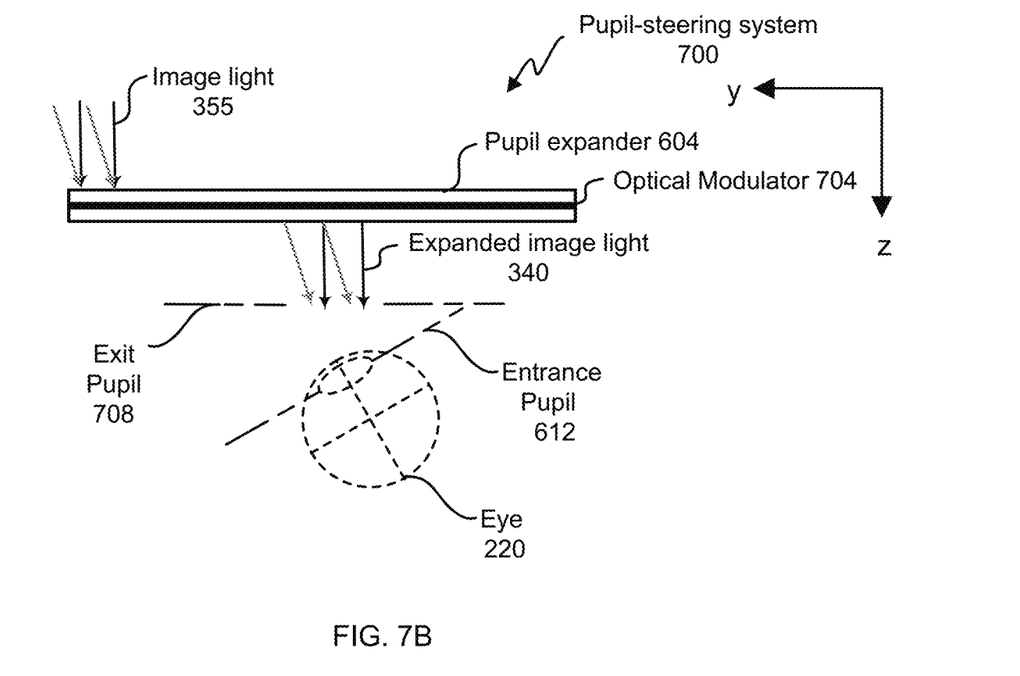
FIG. 7B is another simplified embodiment of the pupil expander with pupil steering.

FIG. 7B is a simplified embodiment of the pupil-steering system 700 with the eye 220 at a different gaze angle than in FIG. 7A. The eye 220 has turned left in the drawing (positive y-direction, or "up"). Accordingly, the exit pupil 708 in FIG. 7B has shifted left in the drawing (positive y-direction, or "up") and narrowed as compared to the exit pupil 708 in FIG. 7A For other field angles, the exit pupil 708 could remain the same size or expand.

Figure 8:
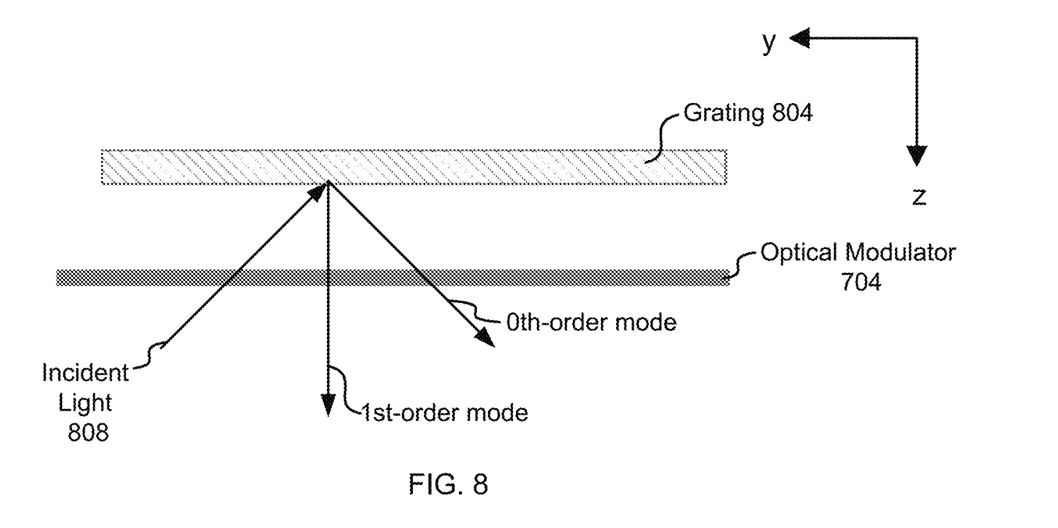
FIG. 8 is a simplified embodiment of an optical modulator changing diffraction efficiency of light incident on a grating.

FIG. 8 is a simplified embodiment of an optical modulator 704 changing diffraction efficiency of light incident on a grating 804. The grating 804 is a diffraction grating. The grating 804 can be used as the decoupling element 365 or as part of the decoupling element 365. Incident light 808 propagates toward the grating 804. Before reaching the grating 804, the incident light 808 passes through the optical modulator 704. The optical modulator 704 manipulates a property of the incident light 808. For example, the optical modulator 704 can manipulate a polarization of the incident light 808. The optical modulator 704 is configured to modulate the incident light 808 to spatially change diffraction efficiency of the incident light 808 on the grating 804.

Diffraction efficiency is a percentage of light that is diffracted into a mode of the grating 804. Diffraction efficiency of a reflective, diffraction grating is a function of polarization of the incident light 808 (diffraction efficiency can also be a function of other conditions and/or features, such as an angle of the incident light 808). In some embodiments, the optical modulator 704 comprises a liquid crystal (LC) layer. An electrical signal is applied to the LC layer causing liquid crystals to rotate. Rotated liquid crystals can change a polarization of the incident light 808. Polarization of the incident light 808 can be modulated spatially. Changing polarization of the incident light 808 does not attenuate the incident light 808.

The incident light 808 can be diffracted into a zeroth-order mode (0th-order mode), a first-order mode (1st-order mode), and/or higher-order modes. The grating 804 can be designed to diffract light primarily into the zeroth-order mode and the first-order mode (i.e., designed to reduce diffraction into modes higher than the first-order mode). Depending on polarization of the incident light 808, the incident light 808 will be diffracted into the zeroth-order mode and/or the first-order mode. If the incident light 808 has a first polarization, the incident light 808 is diffracted in the zeroth-order mode (e.g., equal to or greater than 50, 75, 80, 90, or 95% of light is diffracted in the zeroth-order mode). If the incident light 808 has a second polarization, the incident light 808 is diffracted in the first-order mode (e.g., equal to or greater than 50, 75, 80, 90, or 95% of light is diffracted in the first-order mode). In some embodiments, the incident light 808 is linearly polarized and/or elliptically polarized (e.g., having a major axis that is equal to or greater than 1.5, 2, 3, or 10 times a minor axis). The LC layer can rotate polarization of the major axis of elliptically-polarized light (e.g., by 30 degrees or more and/or by less than 180 degrees). Thus by changing the LC layer, polarization of incident light 808 can be changed, which changes the diffraction efficiency of the incident light 808 on the grating 804 between the zeroth-order mode and the first-order mode of the grating 804.

Figure 9:
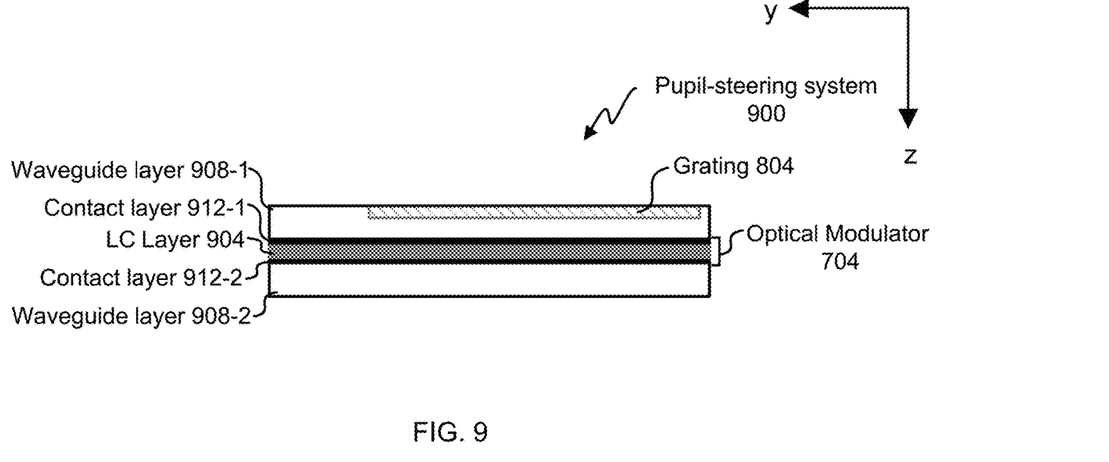
FIG. 9 is a simplified embodiment of an optical modulator as part of a waveguide pupil expander.

FIG. 9 is a simplified embodiment of an optical modulator as part of a waveguide pupil expander of a pupil-steering system 900. The pupil-steering system 900 comprises a grating 804, an LC layer 904, a first waveguide layer 908-1, a second waveguide layer 908-2, a first contact layer 912-1, and a second contact layer 912-2. The LC layer 904, the first contact layer 912-1, and the second contact layer 912-2 are part of the optical modulator 704. The LC layer 904 is between the first waveguide layer 908-1 and the second waveguide layer 908-2. The first waveguide layer 908-1 and the second waveguide layer 908-2 are configured to guide light as an output waveguide 320. In some embodiments, the waveguide layers 908 are made of a transparent material, such as glass or polycarbonate (e.g., transparent to visible wavelengths of light, wherein transparent is transmission of greater than 70, 80, 90, 95, or 98%).

The grating 804 is formed in the first waveguide layer 908-1, but the grating 804 could be formed in the second waveguide layer 908-2, or in another layer next to the first waveguide layer 908-1 or the second waveguide layer 908-2. The grating 804 is a diffraction grating configured to decouple light from the pupil-steering system 900. Light diffracted in a first-order mode of the grating 804 is decoupled from the pupil-steering system 900, and light diffracted in the zeroth-order mode of the grating 804 continues to be guided by the waveguide layers 908 in the pupil-steering system 900.

The LC layer 904 changes polarization of incident light 808. The LC layer 904 is modulated spatially to decouple light from only a portion of the pupil-steering system 900. In some embodiments, there are multiple layers of liquid crystals in the LC layer 904 and/or multiple LC layers 904 (e.g., two LC layers 904 to give more control of light modulation). The LC layer 904 is index matched with the first waveguide layer 908-1 and/or with the second waveguide layer 908-2.

The first contact layer 912-1 is between the LC layer 904 and the first waveguide layer 908-1. The second contact layer 912-2 is between the LC layer 904 and the second waveguide layer 908-2. The first contact layer 912-1 and the second contact layer 912-2 provide electrical contacts to the LC layer 904. Electrical signals are transmitted through the first contact layer 912-1 and/or the second contact layer 912-2 to modulate the LC layer 904. In some embodiments, the electrical signals are variable signals (e.g., not binary), to rotate liquid crystals to variable states. The first contact layer 912-1 and/or the second contact layer 912-2 are made of indium tin oxide (ITO) (e.g., so that the contact layers 912 are transparent). By applying electrical signals to the first contact layer 912-1 and/or to the second contact layer 912-2, diffraction efficiency to the first-order mode can be reduced (e.g., to less than 30, 20, 10, 5, or 2%). In some embodiments, by applying electrical signals to the first contact layer 912-1 and/or to the second contact layer 912-2, diffraction efficiency to the first-order mode can be increased (e.g., depending on initial light polarization and/or structure of the grating 804).

In some embodiments, an optical modulator comprises: a first layer (e.g., the first waveguide layer 908-1), wherein the first layer is transparent to visible wavelengths of light; a second layer (e.g., the second waveguide layer 908-2), where the second layer is transparent to visible wavelengths of light; and a third layer (e.g., LC layer 904), wherein the third layer is between the first layer and the second layer, and the third layer comprises liquid crystals. The first layer and the second layer can be glass. The optical modulator can comprise one or more electrical paths (e.g., in the first contact layer 912-1 and/or the second contact layer 912-2) configured to transmit one or more electrical signals to the third layer to change orientation of the liquid crystals, wherein changing orientation of the liquid crystals is used to modulate light incident on the grating 804. The electrical paths can be stripes of indium tin oxide patterned on the first layer. The grating 804 can be formed in the first layer. The first layer and the second layer can form an optical waveguide of a pupil expander for a near-eye display, and/or the grating is part of a decoupling element for the near-eye display.

Figure 10:
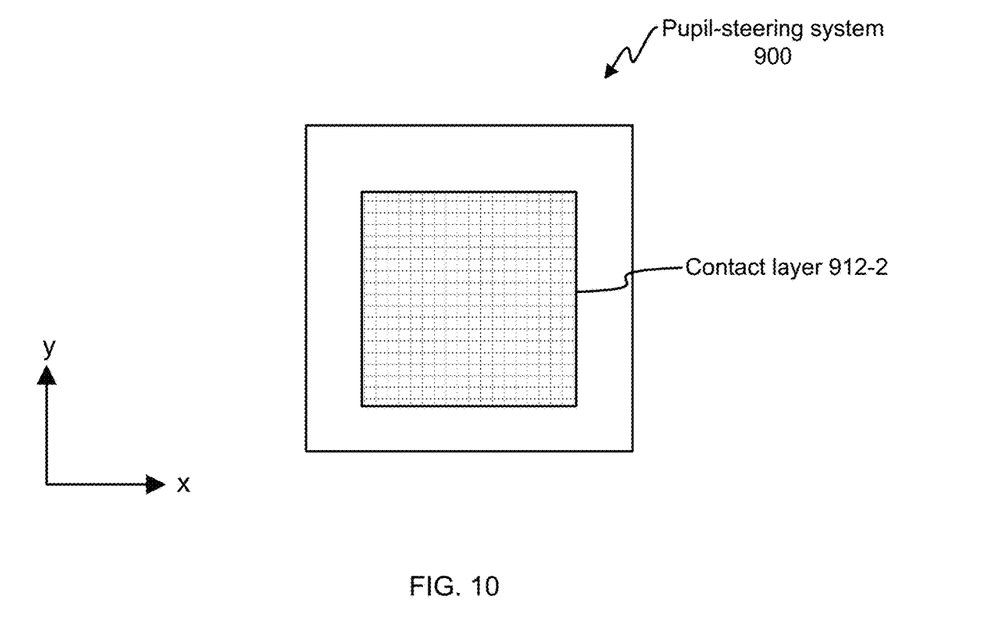
FIG. 10 illustrates an embodiment of wire paths for an optical modulator.

FIG. 10 illustrates an embodiment of wire traces of a contact layer 912 in an optical modulator 704. FIG. 10 depicts the pupil-steering system 900 and the second contact layer 912-2 (the first contact layer 912-1 can overlap the second contact layer 912-2). The contact layer 912 comprises a plurality of electrical paths (e.g., wires). The contact layer 912 can be made fine enough (e.g., spacing between parallel electrical paths of the contact layer 912) to control a pixel of the waveguide display assembly 210. The first contact layer 912-1 can be applied to the first waveguide layer 908-1 and/or the second contact layer 912-2 can be applied to the second waveguide layer 908-2 (e.g., stripes of indium tin oxide patterned on a waveguide layer 908). An addressable modulation scheme is used to spatially activate the LC layer 904 using the contact layers 912.

Figure 11A:
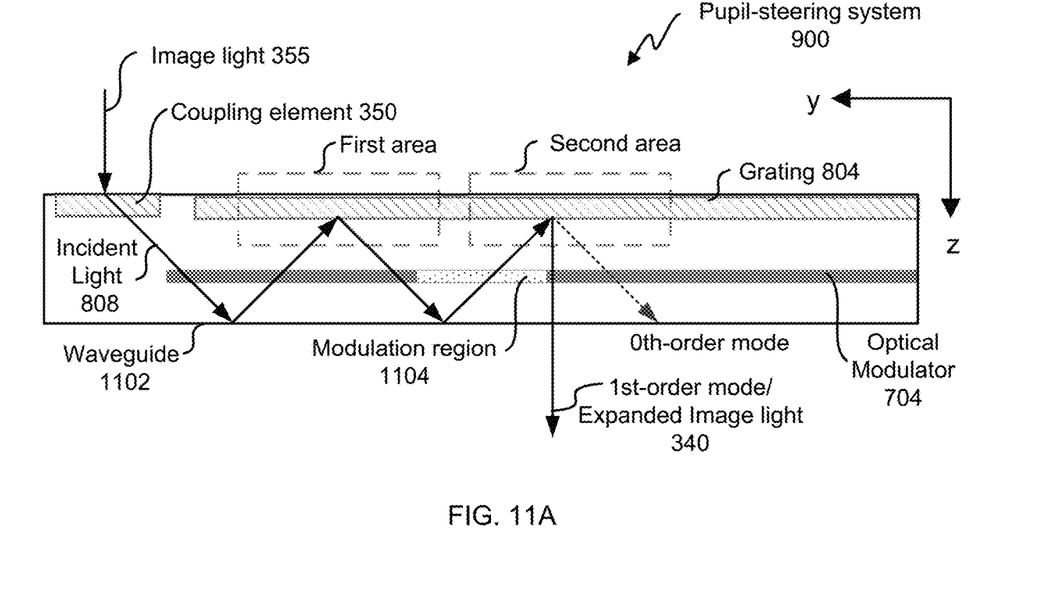
FIG. 11A illustrates an embodiment of a modulator spatially varying incident light to change efficiency of a grating.

FIG. 11A illustrates an embodiment of an optical modulator 704 spatially varying incident light 808 to change diffraction efficiency of light incident on the grating 804. FIG. 11A shows an embodiment of the pupil-steering system 900. The source assembly 310 emits image light 355. The source assembly 310 is an optical source. Image light 355 is coupled into a waveguide 1102 (e.g., comprising waveguide layers 908) of the pupil-steering system 900 by the coupling element 350. Light is coupled out of the waveguide by a decoupling element (e.g., grating 804). The optical modulator 704 is configured to modulate light incident on the decoupling element to spatially change decoupling of light out of the pupil-steering system 900.

Image light 355 entering the waveguide can have a preferred, deterministic polarization after passing through the coupling element 350. Image light 355 coupled into the waveguide is guided in the waveguide (e.g., using the first waveguide layer 908-1 and the second waveguide layer 908-2). Image light 355 coupled into the waveguide becomes incident light 808. The incident light 808 is modulated by the optical modulator 704 so that there is lower diffraction efficiency of incident light 808 to couple into the first-order mode at a first area of the grating 804. The incident light 808 is modulated so that there is higher diffraction efficiency of the incident light 808 coupled into the first-order mode at a second area of the grating 804. For example, a modulation region 1104 changes polarization of incident light 808, before the incident light 808 propagates to the second area of the grating 804, so that the incident light 808 is more strongly coupled into the first-order mode and decoupled from the waveguide as expanded image light 340. As the eye 220 moves, the modulation region 1104 also moves (e.g., spatially in x and/or y) and/or changes in size (e.g., gets larger or smaller).

The modulation region 1104 can be configured to change polarization of incident light 808 to couple more strongly into the first-order mode (e.g., so that less power is used to modulate the LC layer 904 since an area of modulation for decoupling is likely smaller than an area that is not decoupled). The modulation region 1104 can also be configured to change polarization of incident light 808 to couple more strongly into the zeroth-order mode (e.g., so that if pupil steering fails, the waveguide display assembly 210 reverts to a pupil expander 604 with the exit pupil 608).

In some embodiments, an apparatus comprises the waveguide 1102, the coupling element 350, and a decoupling element. The coupling element 350 is configured to couple light into the waveguide 1102. The decoupling element comprises the grating 804 and the optical modulator 704, wherein the optical modulator can be an optical element configured to vary polarization of light incident on the grating 804. The decoupling element is configured to output light from the waveguide 1102 toward an eye 220 of a user of the apparatus from a selected location of the decoupling element and/or in a selected orientation from the decoupling element; and to vary the selected location and/or the selected orientation in response to tracking of the eye of the user. The selected location can vary based changing the modulation region 1104 of the optical modulator 704. For example, the selected location in FIG. 11A is the second area. In some embodiments, the apparatus comprises an eye-tracking module, which can be configured to track a position of the pupil of the eye 220 and/or an orientation of the eye 220.

In some embodiments, the optical element comprises liquid-crystals; the optical element is configured to vary polarization of light incident on the grating so that there is higher diffraction efficiency for light incident on the first area of the grating than for light incident on the second area of the grating; light outputted by the decoupling element from the selected location and/or in the selected orientation defines an exit pupil that is slightly larger than a pupil of the eye; the exit pupil is equal to or greater than a width of the pupil of the eye and equal to or less than two times the width of the pupil of the eye; light outputted by the decoupling element from the selected location and/or in the selected orientation defines an exit pupil of the apparatus that is substantially smaller than the decoupling element; the exit pupil is less than one fourth of the decoupling element; and/or the exit pupil is less than one fourth of the decoupling element. The exit pupil 708 being slightly larger than the pupil of the eye can mean that a width of the exit pupil 708 is equal to or greater than a width of the entrance pupil 612 and equal to or less than 1.2, 1.5, 1.75, and or 2 times the width of the entrance pupil 612. The exit pupil 708 being substantially smaller than the decoupling element can mean that the exit pupil 708 has an area that is equal to or less than ½, ¼, ⅛, 1/16, or 1/32 of an area of the exit pupil 608 and/or equal to or greater than an area of the entrance pupil 612.

In some embodiments a system comprises a source (e.g., source 410), wherein the source is an optical source; a waveguide (e.g., waveguide 1102); a coupling element (e.g., coupling element 350), wherein the coupling element is configured to couple light from the source into the waveguide; and a decoupling element, the decoupling element is configured to: couple light out of the waveguide and toward an eye of a user of the system from a selected location of the decoupling element and/or in a selected orientation from the decoupling element, and vary the selected location and/or the selected orientation in response to tracking of the eye of the user. The system can comprise a frame (e.g., frame 105), wherein the frame is part of glasses to be worn by the user, and the waveguide, the coupling element, and the decoupling element are part of a lens secured in the frame.

Figure 11B:
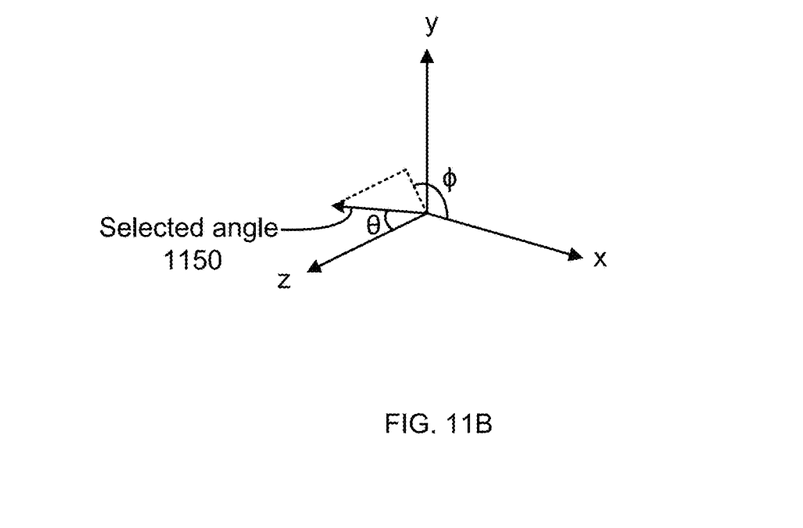
FIG. 11B is a diagram of an embodiment of light emitted from a decoupling element at a selected angle.

FIG. 11B is a diagram of an embodiment of light emitted from a decoupling element at a selected angle 1150. The selected angle 1150 can be measured in spherical coordinates with an azimuth angle phi $\phi$ and a polar angle theta $\theta$. The azimuth angle in measured in the x/y plane from the x axis, wherein the x/y plane is parallel to a flat surface of the waveguide 1102 and/or parallel to the grating 804. The polar angle is measured from the z axis. Orientation of expanded image light 340 is a function of incident angle of image light 355 on the coupling element 350. In some embodiments, the selected angle 1150 is an orientation of expanded image light 340 corresponding to image light 355 being coupled into the coupling element 350 at normal incidence (e.g., at 90 degrees to a surface of the coupling element 350 and/or parallel to the z axis). In FIG. 11B, the azimuthal angle can range from zero to 360 degrees, and the polar angle can range from zero to 90 degrees. The selected angle 1150 is also a function of physical properties of the grating 804 and/or polarization of light incident on the grating 804.

Figure 12:
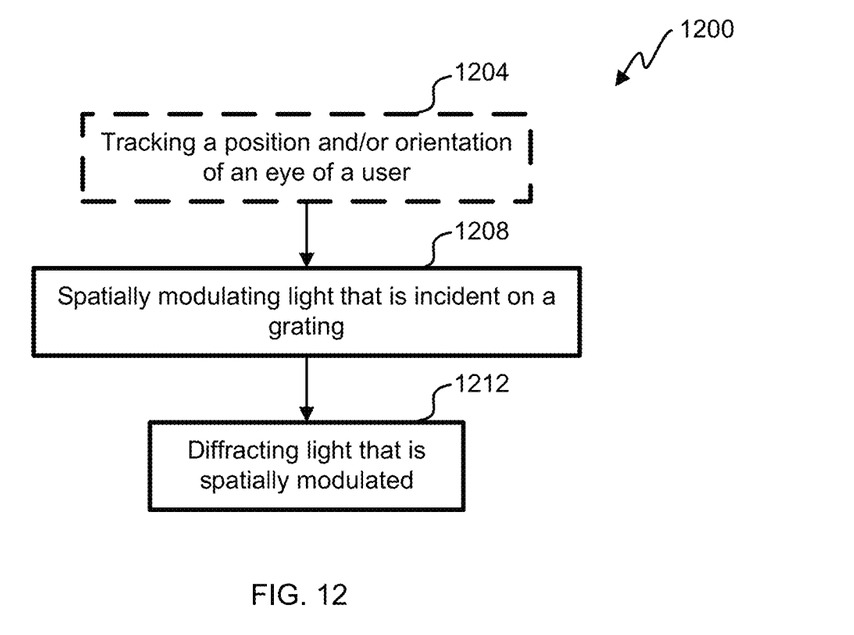
FIG. 12 illustrates a flowchart of an embodiment of a process for beam steering in a pupil expander.

FIG. 12 illustrates a flowchart of an embodiment of a process 1200 for beam steering with a pupil expander 604. Process 1200 begins in step 1204 with tracking a position and/or an orientation of an eye of a user (e.g., the eye 220 is tracked). In step 1208, light that is incident on a grating is spatially modulated based on tracking the eye of the user. For example, the optical modulator 704 changes polarization of light as a function of x and/or y to decouple light from the pupil-steering system 700 at the exit pupil 708. The exit pupil 708 can be steered around in x and y as the eye 220 moves.

In step 1212, light, which is spatially modulated, is diffracted by a grating (e.g., grating 804). There is lower diffraction efficiency (e.g., diffraction efficiency to the first-order mode) for light incident on a first area of the grating 804 than for light incident on a second area of the grating 804 (e.g., see FIG. 11A). Diffraction efficiency is between the zeroth-order mode and the first-order mode of the grating 804.

In some embodiments, step 1204 is not used. For example, the exit pupil 708 could be manually adjusted (e.g., size and/or location) by a user to change inter pupil distance of the near-eye display 100. Thus the pupil-steering system could be used to electrically adjust for inter-pupillary distance instead of mechanically adjusting for inter-pupillary distance.

Figure 13:
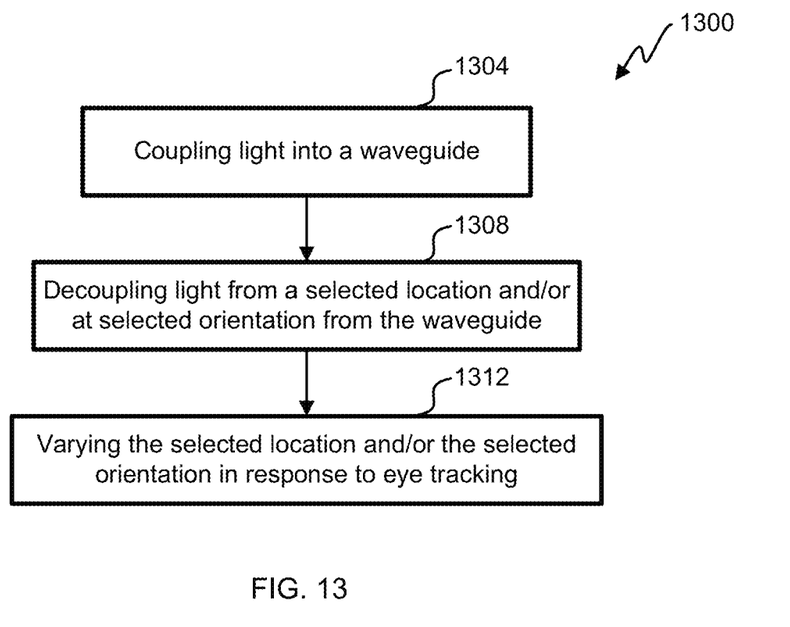
FIG. 13 illustrates another flowchart of an embodiment of a process for beam steering.

FIG. 13 illustrates a flowchart of an embodiment of a process 1300 for beam steering. Process 1300 begins in step 1304 with coupling light into the waveguide 1102 using the coupling element 350. In step 1308, light is decoupled, using a decoupling element, from a selected location of the decoupling element and/or in a selected orientation from the decoupling element toward the eye 220. In step 1312, the selected location and/or the selected orientation is varied in response to tracking of the eye 220. The eye 220 can be tracked by a tracking module.

In some embodiments, the process 1300 can comprise varying polarization of light incident on the grating 804 (e.g., using optical modulator 704) so that there is higher diffraction efficiency for light incident on a second area of the grating than for light incident on a first area of the grating, wherein the second area is the selected location. The terms "first" and "second" are used to differentiate between similar terms and are not necessarily meant to imply a specific order. In some embodiments, the process 1300 comprises: modulating electrical signals to a liquid crystal layer to vary polarization of light passing through the liquid crystal layer to vary the selected location and/or the selected orientation; and/or tracking a location of a pupil of the eye, and spatially modulating light based on tracking the location the pupil. Is some embodiments varying polarization comprises rotating light polarization by 30 degrees or more and less than 180 degrees; and/or diffraction efficiency is higher for more light to couple into a first-order mode of the grating than coupling into a zeroth-order mode grating.

In some embodiments, diffraction efficiency is higher for more light to couple into a first-order mode of a grating than coupling into a zeroth-order mode of the grating; spatially modulating light comprises changing polarization of light; spatially modulating light comprises modulating electrical signals to a liquid crystal layer such that an exit pupil of an optical system is smaller than a potential exit pupil area of the optical system; the exit pupil is steerable within the potential exit pupil area based on eye tracking; and/or the optical system comprises the grating and the liquid crystal layer. In some embodiments, a method comprises tracking a position and/or orientation of an eye of a user; spatially modulating light based on tracking the position and/or orientation of the eye of the user; tracking a location of a pupil of the eye; spatially modulating light based on tracking the location the pupil; tracking a position and/or orientation of an eye of a user; and/or spatially modulating light based on tracking the position and/or orientation of the eye of the user.

Embodiments of the invention may include or be implemented in conjunction with an artificial reality system. Artificial reality is a form of reality that has been adjusted in some manner before presentation to a user, which may include, e.g., a virtual reality (VR), an augmented reality (AR), a mixed reality (MR), a hybrid reality, or some combination and/or derivatives thereof. Artificial reality content may include completely generated content or generated content combined with captured (e.g., real-world) content. The artificial reality content may include video, audio, haptic feedback, or some combination thereof, and any of which may be presented in a single channel or in multiple channels (such as stereo video that produces a three-dimensional effect to the viewer). Additionally, in some embodiments, artificial reality may also be associated with applications, products, accessories, services, or some combination thereof, that are used to, e.g., create content in an artificial reality and/or are otherwise used in (e.g., perform activities in) an artificial reality. The artificial reality system that provides the artificial reality content may be implemented on various platforms, including a head-mounted display (HMD) connected to a host computer system, a standalone HMD, a mobile device or computing system, or any other hardware platform capable of providing artificial reality content to one or more viewers.

The foregoing description of the embodiments of the disclosure has been presented for the purpose of illustration; it is not intended to be exhaustive or to limit the disclosure to the precise forms disclosed. Persons skilled in the relevant art can appreciate that many modifications and variations are possible in light of the above disclosure.

Some portions of this description describe the embodiments of the disclosure in terms of algorithms and symbolic representations of operations on information. These algorithmic descriptions and representations are commonly used by those skilled in the data processing arts to convey the substance of their work effectively to others skilled in the art. These operations, while described functionally, computationally, or logically, are understood to be implemented by computer programs or equivalent electrical circuits, microcode, or the like. Furthermore, it has also proven convenient at times, to refer to these arrangements of operations as modules, without loss of generality. The described operations and their associated modules may be embodied in software, firmware, and/or hardware.

Steps, operations, or processes described may be performed or implemented with one or more hardware or software modules, alone or in combination with other devices. In some embodiments, a software module is implemented with a computer program product comprising a computer-readable medium containing computer program code, which can be executed by a computer processor for performing any or all of the steps, operations, or processes described.

Embodiments of the disclosure may also relate to an apparatus for performing the operations described. The apparatus may be specially constructed for the required purposes, and/or it may comprise a general-purpose computing device selectively activated or reconfigured by a computer program stored in the computer. Such a computer program may be stored in a non-transitory, tangible computer readable storage medium, or any type of media suitable for storing electronic instructions, which may be coupled to a computer system bus. Furthermore, any computing systems referred to in the specification may include a single processor or may be architectures employing multiple processor designs for increased computing capability.

Embodiments of the disclosure may also relate to a product that is produced by a computing process described herein. Such a product may comprise information resulting from a computing process, where the information is stored on a non-transitory, tangible computer readable storage medium and may include any embodiment of a computer program product or other data combination described herein.

The language used in the specification has been principally selected for readability and instructional purposes, and it may not have been selected to delineate or circumscribe the inventive subject matter. It is therefore intended that the scope of the disclosure be limited not by this detailed description, but rather by any claims that issue on an application based hereon. Accordingly, the disclosure of the embodiments is intended to be illustrative, but not limiting, of the scope of the disclosure, which is set forth in the following claims.

What is claimed is:

1. An apparatus comprising:
   a waveguide;
   a coupling element configured to couple light into the waveguide; and
   a decoupling element configured to:
     output light from the waveguide toward an eye of a user of the apparatus from a selected location of the decoupling element and/or in a selected orientation from the decoupling element; and
     vary the selected location and/or the selected orientation in response to tracking of the eye of the user.

2. The apparatus of claim 1, wherein the decoupling element comprises:
   a grating; and
   an optical element configured to vary polarization of light incident on the grating.

3. The apparatus of claim 2, wherein the optical element comprises liquid-crystals.

4. The apparatus of claim 1, wherein an optical element of the decoupling element is configured to vary polarization of light incident on a grating so that there is higher diffraction efficiency for light incident on a first area of the grating than for light incident on a second area of the grating.

5. The apparatus of claim 1, wherein light outputted by the decoupling element from the selected location and/or in the selected orientation defines an exit pupil that is slightly larger than a pupil of the eye.

6. The apparatus of claim 5, wherein the exit pupil is equal to or greater than a width of the pupil of the eye and equal to or less than two times the width of the pupil of the eye.

7. The apparatus of claim 1, wherein light outputted by the decoupling element from the selected location and/or in the selected orientation defines an exit pupil of the apparatus that is substantially smaller than the decoupling element.

8. The apparatus of claim 7, wherein the exit pupil is less than one fourth of the decoupling element.

9. The apparatus of claim 1, further comprising an eye-tracking module configured to track a location of a pupil of the eye, and wherein the decoupling element is configured to vary the selected location and/or the selected orientation based on tracking the location of the pupil.

10. The apparatus of claim 1 further comprising an eye-tracking module configured to track an orientation of the eye, and wherein the decoupling element is configured to vary the selected location and/or the selected orientation based on tracking the orientation of the eye.

11. A method comprising:
   coupling, using a coupling element, light into a waveguide;

decoupling light, using a decoupling element, from a selected location of the decoupling element and/or in a selected orientation from the decoupling element toward an eye; and varying the selected location and/or the selected orientation in response to tracking of the eye.

12. The method of claim 11, further comprising tracking the eye.

13. The method of claim 11, further comprising varying polarization of light incident on a grating so that there is higher diffraction efficiency for light incident on a first area of the grating than for light incident on a second area of the grating, wherein the first area is the selected location.

14. The method of claim 13, wherein diffraction efficiency is higher where more light is coupled into a first-order mode of the grating than coupled into a zeroth-order mode of the grating.

15. The method of claim 11, further comprising modulating electrical signals to a liquid crystal layer to vary polarization of light passing through the liquid crystal layer to vary the selected location and/or the selected orientation.

16. The method of claim 15, wherein varying polarization comprises rotating light polarization by 30 degrees or more and less than 180 degrees.

17. The method of claim 11, further comprising:
tracking a location of a pupil of the eye; and
spatially modulating light based on tracking the location the pupil.

18. The method of claim 11, further comprising:
tracking an orientation of an eye; and
spatially modulating light based on tracking the orientation of the eye.

19. A system comprising:
a source, wherein the source is an optical source;
a waveguide;
a coupling element, wherein the coupling element is configured to couple light from the source into the waveguide; and
a decoupling element, the decoupling element configured to:
couple light out of the waveguide and toward an eye of a user of the system from a selected location of the decoupling element and/or in a selected orientation from the decoupling element; and
vary the selected location and/or the selected orientation in response to tracking of the eye of the user.

20. The system of claim 19, further comprising a frame, wherein:
the frame is part of glasses to be worn by the user; and
the waveguide, the coupling element, and the decoupling element are part of a lens secured in the frame.

\* \* \* \* \*